United States Patent [19]

Slavin

[11] Patent Number: 6,143,292
[45] Date of Patent: Nov. 7, 2000

[54] ALLOGENEIC CELL THERAPY FOR CANCER FOLLOWING ALLOGENEIC STEM CELL TRANSPLANTATION

[75] Inventor: Shimon Slavin, Jerusalem, Israel

[73] Assignees: Baxter International Inc., Deerfield, Ill.; Hadasit Medical Research Services and Development Ltd., Jerusalem, Israel

[21] Appl. No.: 08/930,071

[22] PCT Filed: May 24, 1996

[86] PCT No.: PCT/US96/07652

§ 371 Date: Nov. 21, 1997

§ 102(e) Date: Nov. 21, 1997

[87] PCT Pub. No.: WO96/37208

PCT Pub. Date: Nov. 28, 1996

Related U.S. Application Data

[63] Continuation-in-part of application No. 08/449,764, May 25, 1995, abandoned.

[51] Int. Cl.[7] .............................. A61K 35/28; C12N 5/08
[52] U.S. Cl. ................... 424/93.7; 424/93.71; 424/85.5; 424/85.7; 424/85.2; 424/85.4; 424/144.1; 424/577; 424/578; 435/325; 435/375
[58] Field of Search ............................. 424/93.71, 93.7, 424/85.5, 85.7, 85.2, 85.4, 144.1, 577, 578; 435/325, 372

[56] References Cited

FOREIGN PATENT DOCUMENTS

WO 91/12849  9/1991  WIPO .
WO 95/24910  9/1995  WIPO .

OTHER PUBLICATIONS

Slavin et al., *Leukemia* 6:164–166 (1992).
Slavin et al., *Bone Marrow Transplant.* 12:S54–S56 (1993).
Slavin et al., 19th Annual Meeting of the EBMT and 9th Meeting of the Nurses Group, Abstracts, MMV Medinzin Verlag GmbH, Munich, ISBN 3–8208–1199–0; 48 (Abstract 1601) (1993).
Slavin et al., *Blood* 82:423a (Abstract 1677) (1993).
Slavin et al., *Bone Marrow Transplant.* 4:80–81 (1988).
Naparstek et al., *Experimental Hematology* 21:1061 (Abstract 189) (1993).
Weiss et al., *Cancer Immunol. Immunother.* 31:236–242 (1990).
Slavin et al., *Haematology and Blood Transfusion* 33:36–40 (1990).
J. Antin, *Blood* 82:2273–2277 (1993).
Bär et al., *J. Clin. Oncology* 11:513–519 (1993).
Collins et al., *Blood* 82:417a (Abstract 1652) (1993).
De Witte et al., *Exp. Hematol.* 20:723 (Abstract 71) (1992).
Drobyski et al., *Bone Marrow Transplantation* 10:301–304 (1992).
Drobyski et al., *Blood* 82:2310–2318 (1993).
Frassoni et al., *Exp. Hematol.* 20:712 (Abstract 30) (1992).
Helg et al., *Bone Marrow Transplantation* 12:125–129 (1993).
Hertenstein et al., *Transplantation* 56:1114–1118 (1993).
Jiang et al., *Bone Marrow Transplantation* 11:133–138 (1993).
Johnson et al., *Bone Marrow Transplantation* 11:329–336 (1993).
Kolb et al., 19th Annual Meeting of EBMT, Eur. Group Bone Marrow Transplant (Abstract 1605) (1993).
Kolb et al., *Blood* 82:214a (Abstract 840) (1993).
Leber et al., *Bone Marrow Transplantation* 12:405–407 (1993).
Novotny et al., Chronic Myeloid Leukemia Second International Conference (Abstract 277) (1992).
Porter et al., *N. Engl. J. Med.* 330:100–106 (1994).
van Rhee et al., *Blood* 82:416a (Abstract 1650) (1993).
van Rhee et al., *Blood* 83:3377–3383 (1994).
Szer et al., *Bone Marrow Transplantation* 11:109–111 (1993).
Slavin et al., *Cancer Investigation* 10:221–227 (1992).
Delain et al., *Leukemia* 8:642–647 (1994).
Marmont, *Leukemia and Lymphoma*, 11:221–226 (1992).
Ackerstein et al., *Blood* 974a (Abstract 3886) (1995).
Slavin et al., *Blood* 87:2195–2204 (1996).
Buzyn–Veil, *British Journal of Haematology* 92:423–425 (1996).
Giralt et al., *Blood* 8:4337–4343 (1995).

*Primary Examiner*—Phuong T. Bui
*Attorney, Agent, or Firm*—Townsend and Townsend and Crew LLP

[57] ABSTRACT

A method of treating a human cancer patient having a solid tumor comprising malignant cells is disclosed, wherein the patient having undergone a cancer therapy regimen comprising allogeneic stem cell transplantation. The method comprises administering allogeneic lymphocytes to the patient and monitoring the patient for levels of malignant cells.

16 Claims, 8 Drawing Sheets

ALLOGENEIC CELL THERAPY FOR CANCER FOLLOWING ALLOGENEIC STEM CELL TRANSPLANTATION

This is a continuation in part of U.S. application Ser. No. 08/449,764, filed May 25, 1995, now abandoned.

FIELD OF THE INVENTION

This invention relates to a methods for eradicating tumor cells that remain viable in a patient following allogeneic stem cell transplantation. More particularly, this invention relates to use of allogeneic lymphocytes for eradication of solid tumor cells following allogeneic stem cell transplantation. The invention also relates specifically to use of allogeneic activated donor lymphocytes for treatment of cancer patients, including relapsing patients.

BACKGROUND OF THE INVENTION

Patients suffering from malignant hematological disorders such as leukemia or lymphoma may, under appropriate circumstances, be administered autologous or allogeneic bone marrow transplants as part of a therapeutic regimen. Such transplants also can be useful in conjunction with therapy of non-hematological malignancies such as breast carcinomas or other solid tumors. Bone marrow transplantation makes it possible to administer to patients with resistant disease high, "supra-lethal," combinations of chemotherapy and/or radiation, ignoring the irreversible toxicity of such therapeutic combinations on the normal bone marrow compartment. Nevertheless, such "debulking" of a patient's tumor can leave a fraction of residual malignant cells that may lead to disease relapse.

Several lines of evidence suggest that a significant proportion of the beneficial effect of allogeneic bone marrow transplantation (i.e., bone marrow transplantation from an individual not genetically identical to the host patient) stems from cell-mediated interactions of immune cells of donor origin against residual tumor cells in the host that have escaped the chemoradiotherapy debulking regimen. Following allogeneic bone marrow transplantation (Allo-BMT), the incidence of relapse is significantly lower in leukemia patients with clinical manifestations of acute or chronic graft versus host disease (GVHD), as compared with patients with no GVHD, indicating that immune-mediated allogeneic interactions of immunocompetent cells of donor origin against the host can be accompanied by graft vs. leukemia (GVL) effects.

Higher relapse rates seem to occur in patients undergoing Allo-BMT with T-lymphocyte depletion for prevention of GVHD, compared to recipients of non-T-cell depleted marrow allografts, regardless of the severity of GVHD. Likewise, relapse rates in patients with acute leukemia or chronic myelogenous leukemia reconstituted by bone marrow grafts obtained from an identical twin (syngeneic grafts) are significantly higher than in those reconstituted by bone marrow cells obtained from an HLA-identical but non-syngeneic sibling. Similarly, relapse rates following transplantation of the patient's own (autologous) marrow, even following adequate purging in vitro for elimination of residual leukemia cells, are significantly higher than following Allo-BMT.

Recent studies by several groups have demonstrated that chronic myelogenous leukemia (CML) patients who relapse following Allo-BMT can be treated successfully by infusion of resting (i.e., unactivated by in vitro treatment with T-cell activators such as cytokines) HLA-matched leukocytes from the Allo-BMT donor in order to achieve a second remission. Slavin et al., Blood 72 (Suppl. 1): 407a (1988); Kolb et al., Blood 76:2462 (1990); Baer et al., J. Clin. Oncology 11:513 (1993); Jiang et al., Bone Marrow Transpl. 11:133 (1993); Drobyski et al., Blood 82:2310 (1993); Antin, Blood 82:2273 (1993); Porter et al., N. Engl. J. Med. 330:100–06 (1994).

The therapeutic effects of the infused leukocytes are mediated by potentiation of GVL effects, induced following Allo-BMT, by immunocompetent donor T cells that are not tolerant to the malignant hematopoietic cells. Slavin et al., Blood 72 (Suppl. 1): 407a (1988); Slavin et al., Bone Marrow Transpl. 6:155–61 (1990); Kolb et al., Blood 76:2462 (1990); Baer et al., J. Clin. Oncology 11:513 (1993); Jiang et al., Bone Marrow Transpl. 11:133 (1993); Drobyski et al., Blood 82:2310 (1993); Antin, Blood 82:2273 (1993); Porter et al., N. Engl. J. Med. 330:100–06 (1994). Unfortunately, only about 50–70% of the CML patients relapsing post Allo-BMT respond favorably to Allo-CT. Kolb et al., Clin. Blood 82 (Suppl. 1):840 (1993). Moreover, long-term disease free survival is far from optimal due to response failures, subsequent relapse and complications arising from GVHD and marrow aplasia.

Finally, the possible anti-solid tumor effects of allogeneic lymphocytes following Allo-BMT have been relatively unknown compared to the documented effects of allogeneic lymphocytes on malignant hematopoietic cells.

SUMMARY OF THE INVENTION

The present invention includes a method of treating a human cancer patient who has undergone a cancer therapy regimen including allogeneic stem cell transplantation. The term "stem cell transplantation" as used herein includes infusion into a patient of hematopoietic stem cells derived from any appropriate source of stem cells in the body. The stem cells may be derived, for example, from bone marrow, from the peripheral circulation following mobilization from the bone marrow, or from fetal sources such as fetal tissue, fetal circulation and umbilical cord blood. "Bone marrow transplantation" is considered herein to be simply one form of stem cell transplantation. Mobilization of stem cells from the bone marrow can be accomplished, for example, by treatment of the donor with granulocyte colony stimulating factor (G-CSF) or other appropriate factors (e.g., IL-8) that induce movement of stem cells from the bone marrow into the peripheral circulation. Following mobilization, the stem cells can be collected from peripheral blood by any appropriate cell pheresis technique, for example through use of a commercially available blood collection device as exemplified by the CS 3000® Plus blood cell collection device marketed by Baxter Healthcare Corporation. Methods for performing apheresis with the CS 3000® Plus machine are described in Williams et al., Bone Marrow Transplantation 5: 129–33 (1990) and Hillyer et al., Transfusion 33: 316–21 (1993), both publications being incorporated herein by reference.

Infusion of the hematopoietic stem cells may result in complete and permanent engraftment (i.e., 100% donor hematopoietic cells), or may result in partial and transient engrafment, provided the donor cells persist sufficiently long to permit performance of allogeneic cell therapy as described herein. Thus, the term "stem cell transplantation" covers stem cell infusion into a patient resulting in either complete or partial engraftment as described above.

As used herein, the term "Allo-CT" (allogeneic cell therapy) refers to infusion of resting allogeneic lymphocytes, i.e., lymphocytes that have not been previously exposed to T-cell activator in vitro; the term "Allo-ACT" (allogeneic activated cell therapy) refers to infusion of allogeneic lymphocytes preactivated in vitro with a T-cell activator such as recombinant human interleukin-2 (rhIL-2). Such activated donor lymphocytes are herein termed "ADL." It is to be understood that the allogeneic lymphocytes infused into a patient need not be infused as a purified T-cell preparation. Although it is possible to infuse a relatively pure T-cell preparation, the cells may be infused in the form of a peripheral blood mononuclear cell (PBMC) preparation. For example, the PBMC preparation obtained as a result of pheresis with the CS 3000® Plus blood cell collection device is appropriate for the present invention. Such a cell preparation is approximately 95% mononuclear cells, the majority of which are T cells. In appropriate circumstances it is even possible to administer allogeneic lymphocytes to the patient by simply providing whole blood.

Both Allo-CT and Allo-ACT may be performed with or without accompanying in vivo administration of a T-cell activator. Typically the infused allogeneic lymphocytes are derived from the same donor who provided the stem cells for allogeneic stem cell transplantation. However, the infused lymphocytes may be derived from other donors in appropriate circumstances. For example, if the infused lymphocytes are lifespan-limited as described below, the same or a different donor can provide the cells, depending on the clinical setting.

The term "cancer" as used herein includes all pathological conditions involving malignant cells; this can include "solid" tumors arising in solid tissues or organs (i.e., tumor cells growing as multi-cellular masses supported by blood vessels), as well as tumor cells originating from hematopoietic stem cells.

The invention features a method of treating human cancer patients with solid tumors, including without limitation breast carcinomas, composed of malignant cells. The patients have undergone allogeneic stem cell transplantation. Post-transplantation, the patients are infused with allogeneic lymphocytes in order to induce a graft-versus-tumor response in the patient. The infused allogeneic lymphocytes can be activated, prior to infusion, by in vitro exposure to a T-cell activator. Whether or not the lymphocytes are activated prior to infusion, the patient also can be provided with T-cell activator in vivo in order to provide continuing activation stimulus to the lymphocytes after infusion.

The T-cell activator comprises at least one T-cell signal transduction pathway activator. The T-cell activator may include, without limitation, one or more of the following signal transduction pathway activators: interleukin-1 (IL-1), interleukin-2 (IL-2) interleukin-4 (IL-4), interleukin-5 (IL-5), interleukin-6 (IL-6), interleukin-7 (IL-7), interleukin-12 (IL-12), interleukin-13 (IL-13), interleukin-15 (IL-15), interferon-alpha (IFNα), interferon-gamma (IFNγ), tumor necrosis factors such as TNFα, anti-CD3 antibodies (anti-CD3), anti-CD28 antibodies (anti-CD28), phytohemagglutinin, concanavalin-A and phorbol esters. The T-cell activators can be native factors obtained from natural sources, factors produced by recombinant DNA technology, chemically synthesized polypeptides or other molecules, or any derivative having the functional activity of the native factor. Most preferably the T-cell activator is IL-2, for example recombinant human IL2 (rhIL-2). The T-cell activator used to activate the donor lymphocytes in vitro, and the T-cell activator used for in vivo administration, may be the same or different T-cell signal transduction pathway activators.

The allogeneic lymphocytes may be provided to the patient in a series of incrementally increasing amounts, with the patient monitored for signs of GVHD between increments. If no GVHD manifests, or if the GVHD is not severe and is controllable with standard anti-GVHD prophylaxis, then the patient can be administered an incrementally larger dose of allogeneic lymphocytes than was provided in the previous infusion. Typically, though not necessarily, the dosages are adjusted by log increments, e.g., $10^5$, $10^6$, $10^7$ lymphocytes/kg and so on. Preferably the allogeneic lymphocytes are HLA-compatible (see below) with the patient, although this is not necessary in all cases, particularly if the infused lymphocytes are lifespan-limited. For example, the allogeneic lymphocytes may carry a "suicide gene," allowing the cells to be killed after infusion into the patient, through use of a chemotherapeutic agent. After infusion of the allogeneic lymphocytes, the patient is monitored for levels of malignant cells.

The invention also includes treatment of human cancer patients having malignant hematopoietic cells, for example patients with chronic myelogenous leukemia or acute lymphocytic leukemia. As in the case with solid tumor patients, these patients have undergone an allogeneic stem cell transplantation procedure as part of a regimen to treat the malignancy. Following allogeneic stem cell transplantation, the patient is infused with allogeneic lymphocytes that have been activated in vitro by exposure to a T-cell activator prior to administration to the patient. Following infusion, the patient is monitored for levels of malignant hematopoietic cells. The patient also can be provided with in vivo T-cell activator. The T-cell activator, whether used for in vitro activation or administered in vivo, can be as described above for the solid tumor embodiments.

The present invention is particularly useful for those unfortunate patients who, in spite of an allogeneic stem cell transplant, continue to exhibit malignant cells as evidenced by overt relapse or other indication that malignant cells have not been completely eradicated. The methods are further applicable to patients who have not only failed to respond to an allogeneic stem cell transplant, but who have also failed to respond to a post-transplant cell therapy regimen including infusion of allogeneic resting donor lymphocytes (Allo-CT).

In one embodiment, the patient is administered about $10^5$ cells/kg to about $10^9$ cells/kg of allogeneic ADL and is then monitored for levels of malignant cells. In an alternative embodiment, the patient also can be administered T-cell activator in vivo, for example by injection in concert with a pharmaceutically acceptable carrier. Preferably the T-cell activator is given to the patient over a time course of two to seven days, more preferably two to five days, and most preferably two to four days. The T-cell activator may be administered beginning on the same day as infusion of the allogeneic activated donor lymphocytes.

Preferably the allogeneic donor lymphocytes are HLA-compatible with the patient. HLA-compatible lymphocytes include cells that are fully HLA-matched with the patient. Alternatively the HLA-compatible cells should be at least haploidentical with the patient. If the HLA-compatible lymphocytes are derived from a sibling of the patient, the cells preferably are fully HLA-matched with the patient, although some mismatch may be tolerated. For example, the HLA-compatible lymphocytes from a sibling may, in some cases, be single HLA locus-mismatched. If the HLA-compatible lymphocytes are derived from an unrelated individual, preferably the cells are fully HLA-matched with the patient.

The present invention also includes the use of allogeneic donor lymphocytes, unactivated or in vitro-activated, as well as T-cell activators, in the manufacture of a medicament for the treatment of human cancer patients as described above. The invention further includes an article of manufacture comprising packaging material and a container within the packaging material. The packaging material contains a label or package insert indicating that the contents of the container may be used for the treatment of human cancer patients as described above. The container may be a collapsible container comprising opposing walls of flexible material and a flexible tube protruding from the container. The contents of the container may include unactivated lymphocytes or ADL that are allogeneic with respect to the patient to be treated. Alternatively, the container may include a T-cell activator.

DETAILED DESCRIPTION OF THE INVENTION

Figure 1:
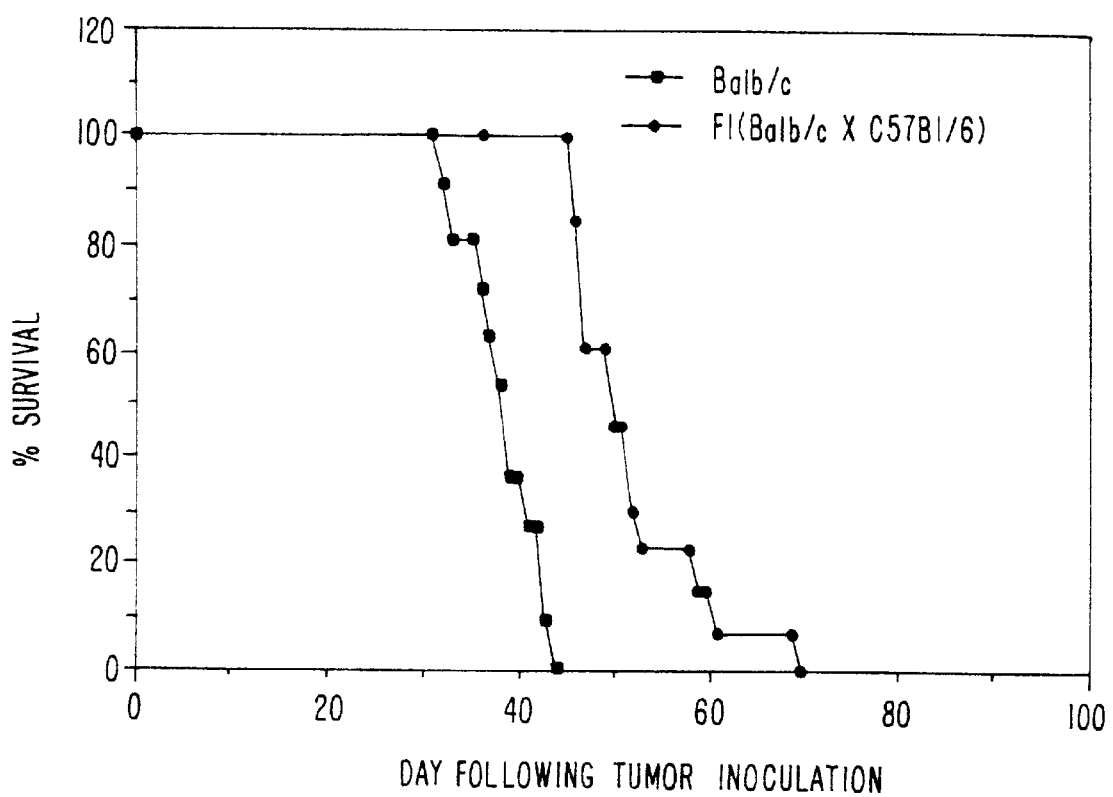
FIG. 1. Percent survival as a function of days following intradermal inoculation of 4T1 tumor cells ($10^4$) into 13 BALB/c or F1 mice in 3 separate experiments per each strain of mice.

A series of animal experiments was undertaken in order to evaluate 1) the ability of allogeneic lymphocytes to effect a solid tumor response following allogeneic stem cell transplantation, and 2) the feasibility and efficacy of Allo-ACT with or without T-cell activator administration in vivo, following allogeneic stem cell transplantation. The concepts developed in the animal experiments were also extended into the clinical setting to demonstrate efficacy in human breast cancer patients as well as with human cancer patients non-responsive to Allo-BMT and Allo-CT.

The animal experiments discussed below demonstrate the feasibility of inducing an immune-mediated graft-versus tumor (GVT) effect in solid tumors, using a murine model of mammary adenocarcinoma derived from BALB/c/(H-$2^d$) mice. A murine breast cancer cell line (4T1) was used that is highly tumorigenic in syngeneic (BALB/c) or haploidentical F1 (BALB/c×C57Bl/6) (F1) mice, is only partially tumorigenic in an H-$2^d$ congenic strain of mice (DBA/2) and is nontumorigenic in an unrelated MHC (H-$2^b$) strain of mice (C57Bl/6). 4T1 cells express on their surfaces class I major histocompatibility (MHC) antigens, adhesion molecules and CD44 homing-associated adhesion molecules, but do not express MHC class II antigens or costimulatory molecules such as B7.

Female BALB/c (H-$2^d$) or F1 (H-$2^{d/b}$) mice were reconstituted with male minor mismatched DBA (H-$2^d$)-derived bone marrow cells or with major mismatched C57 (H-$2^b$)-derived bone marrow cells, respectively, 24 hr following lethal total body irradiation. Recipient mice carrying minor or major mismatched grafted donor cells were inoculated with 4T1 tumor cells 2–3 months following bone marrow reconstitution. The allogeneic donor cells, whether differing from the tumor cells in minor or MHC antigens, were able to affect development of the primary tumor, which expressed host-type MHC alloantigens. Tumor size in bone marrow chimeras across minor or MHC antigens was significantly ($p<0.05$) smaller than tumor size observed in BALB/c or F1 ungrafted control mice. These results demonstrate that it is possible to induce a GVT effect by alloreactive cells in a murine model of mammary carcinoma.

Previous studies (Cohen et al., *J. Immunol.* 151: 1803–10 (1993), incorporated herein by reference) have demonstrated that use of in vitro activated donor lymphocytes (ADL) with or without in vivo rhIL-2 (Allo-ACT±rhIL-2) provides significant GVL effects in mice. However, since 100% survival was observed in all the mice that were administered allogeneic lymphocytes, it was not possible to identify particular enhancements of GVL effects through use of ADL or in vivo rhIL-2. This study also provided confirmation that the GVL effects are caused predominantly by allogeneic T cells and not by natural killer (NK) cells which were considered until recently as being MHC non-restricted. Alloreactive NK cells, B cells and macrophage cells may, however, play a role in the GVL or GVT effects induced by allogeneic T cells. The results further indicated that the GVL effects are not due to the cascade of allogeneic responses, inflammatory reactions and in vivo cytokine release that results from GVHD per se.

In a further set of experiments reported below, BALB/c, C57Bl/6 (B6) and (BALB/c×B6)F1($F_1$) mice were used to evaluate various allogeneic cell therapy protocols accompanied or unaccompanied by in vivo administration of a T-cell activator. BCL1 cells, representing a spontaneous B-cell leukemia/lymphoma of BALB/c origin originally described by Slavin and Strober, Nature 272:624 (1978), were used as a tumor model. Infusion of 10 to 100 BCL1 cells in BALB/c mice results in a typical B cell leukemia/lymphoma characterized by splenomegaly with subsequent peripheral blood lymphocytosis and death in 100% of recipients. BCL1 causes leukemia in $F_1$ recipients also, but takes longer to develop as compared with BALB/c recipients. The present inventor investigated the susceptibility of well-established and fully reconstituted tolerant B6→BALB/c chimeras to BCL1 cells. Chimeras were generated by lethally irradiating BALB/c mice and reconstituting 24 hours later with T-cell depleted B6 bone marrow cells. None of the chimeras showed any clinical evidence of GVHD. Normal BALB/c mice and B6→BALB/c chimeras were injected intravenously with $10^4$, $10^5$, or $10^6$ BCL1 cells. All normal BALB/c mice developed leukemia within 21–58 days and died, whereas all well-established chimeras (i.e., remaining chimeric 2–3 months after induction of chimerism) survived with no evidence of disease for more than 6 months. In contrast, previous studies showed that early inoculation of BCL1 into B6→BALB/c or B6→F1 recipients resulted in leukemia in all recipients with MRD. Weiss et al., Cancer Immunol. Immunother. 31: 236 (1990).

Adoptive transfer experiments were performed with both the normal BALB/c and the B6→BALB/c chimeras that had been injected with $10^6$ BCL1 cells. Spleen cells ($10^5$) were transferred to 10 secondary naive BALB/c mice at 7, 14 and 21 days post-inoculation of the BCL1 cells. Seven out of 10 secondary recipients receiving cells from chimeras removed 7 days after inoculation with BCL1 developed leukemia within 44 days. In contrast, none of the secondary recipients receiving cells obtained from chimeras inoculated with BCL1 cells 14 and 21 days prior to cell transfer developed leukemia. The data suggest that a period of at least 14 days is required for complete eradication of $10^6$ BCL1 cells, whereas at 7 days eradication of leukemic cells is still incomplete.

Further experiments were conducted in the chimeras to determine the effects of in vivo administration of T-cell activator (rhIL-2). Chimeras were injected with $10^6$ BCL1 cells and then variously treated with in vivo rhIL-2, lymphocytes or combinations of rhIL-2 and lymphocytes. After seven days, all the mice were sacrificed and spleen cells were used for adoptive transfer into secondary BALB/c recipients, as above.

All of the secondary BALB/c recipients who received spleen cells from the control normal BALB/c mice developed leukemia. Furthermore, no antileukemic effects were detected in normal control BALB/c mice treated with rhIL-2, allogeneic splenocytes or both. In contrast, 70% of the chimeras in the group without any additional treatment did not develop leukemia for a period greater than 6 months. Of the 30% that developed leukemia, the onset was delayed to 44–52 days. Of the chimeras that received only B6 lymphocytes, 80% remained disease free and the remaining 20% showed delayed onset of leukemia. Of the chimeras that were treated with rhIL-2, or that were treated with both rhIL-2 and B6 lymphocytes, 100% were disease free for more than 6 months.

Taken together, these results indicate that chimeras generated by irradiating BALB/c mice and reconstituting with T-cell depleted B6 bone marrow cells are capable of resisting the leukemogenic potential of BCL1 cells (which are of BALB/c origin), assuming chimerism is established and the recipients are immunocompetent. This is in spite of the fact that the chimeras are fully tolerant to BALB/c alloantigens, since such chimeras have been shown to be fully tolerant to host (BALB/c) alloantigens and to accept donor-type skin allografts indefinitely. Levite and Reisner, Transplantation 55:3 (1993). Moreover, the chimeras are resistant to the BCL1 cells in the absence of GVHD. Thus, the antitumor effects in tolerant chimeras can include recognition of tumor-associated or tumor-specific cell surface determinants other than host-type major histocompatibility complex (MHC) determinants, independently of GVHD. Significantly, enhancement of GVL effects can be achieved, without GVHD or, alternatively, with controllable GVHD, by post-transplant administration of ADL with or without a short course of relatively low-dose rhIL-2.

It is especially advantageous to use graded increments of allogeneic cells while controlling for GVHD. The greater the time interval from BMT to cell therapy, the less likely is the development of uncontrollable GVHD and the larger the number of allogeneic donor T cells that can be given. See Slavin et al., J. Exp. Med. 147: 963 (1978); Slavin et al., Cancer Invest. 10: 221–7 (1992). This may be contrasted to mice with residual tumor cells given allogeneic T cells during the early post-BMT period. The infused allogeneic T cells in these cases do not become tolerant to the host, resulting in GVHD. Thus, infusion of allogeneic lymphocytes, especially following in vitro and in vivo activation of donor T cells by T-cell activators such as rhIL-2, makes it possible to infuse, relatively late post-BMT, non-tumor-tolerant donor T cells that are accepted by the recipient but that engender potent GVL effects. The T cells may be given in graded increments, with proportionately more cells administered as the time from BMT increases.

The results and indications deriving from the mouse experiments were extended into the clinical setting with human patients suffering from breast cancer and from malignant hematological disorders, including acute and chronic leukemias. Specifically, the present inventor has discovered that a therapeutic regimen of Allo-CT can be effective in treating breast cancer following allogeneic BMT. The present inventor has also discovered that activated donor lymphocytes can provide anti-tumor effects even beyond those obtainable with unactivated allogeneic lymphocytes. For example, Allo-ACT and in vivo T-cell activator can be used successfully in a clinical setting to treat relapse following Allo-BMT. Thus, results in human patients provide important confirmation and extension of the animal data reported above.

More particularly, the present inventor has discovered that in vitro activation of donor's PBL prior to infusion into the patient provides a means to induce remission following an unsuccessful regimen of bone marrow transplantation and cellular immunotherapy. Surprisingly, donor's PBL activated in vitro provided a measurable GVL effect when the same cells, absent such in vitro treatment, failed to eradicate the tumor cells. It is noteworthy that, in some cases, these unactivated cells, even though not exposed to T-cell activator prior to infusion, nevertheless were exposed to activating T-cell activator in vivo following infusion. In contrast, PBL from the same donor were effective when preactivated prior to infusion (Allo-ACT approach) and accompanied by in vivo T-cell activator. In addition, it is demonstrated herein that an Allo-ACT regimen can be undertaken in this setting without necessarily inducing clinically significant GVHD.

To document the ability of allogeneic lymphocytes to provide a therapeutic effect in solid tumor patients, a human patient with acute myelogenous leukemia (AML) and recurrent breast cancer was treated with induction chemotherapy, allogeneic stem cell transplantation and post-transplant allogeneic cell therapy (see Example 3 below). The approach in treating this patient was oriented towards AML, although most of the components used for induction chemotherapy are known to be active against breast cancer as well. Nonetheless, the dose intensity was less than optimal for treatment of recurrent breast cancer, and it would not be expected that a patient with an aggressive recurrent breast cancer would respond to such "suboptimal" chemotherapy. The breast cancer response therefore can be attributed to the allogeneic cell-mediated immunotherapy received by this patient.

As an illustrative example to demonstrate the clinical efficacy of the Allo-ACT plus in vivo T-cell activator treatment regimen, a human patient with chronic myelogenous leukemia (CML) having a very poor prognosis was treated (see Patient No. 1 in Example 3, below).

Chronic myelogenous leukemia (CML) is a hematological disorder that is the result of neoplastic transformation of pluripotent stem cells. The Philadelphia (Ph) chromosome was first described in 1960 as an abbreviated chromosome found in the bone marrow of patients with CML. The Ph chromosome is the result of a reciprocal translocation between the long arms of chromosomes 9 and 22. The potential breakpoints on chromosome 22 occur in a small 5.8 kb region called the breakpoint cluster region (bcr). The breakpoint cluster region is part of a large bcr gene that contains four exons. Potential breakpoints on chromosome 9 are scattered over a distance of at least 100 kb, but are all located 5' to the c-abl proto-oncogene. The Ph translocation transfers the c-abl gene from its position on chromosome 9 to the Ph chromosome. Because 90% of CML patients carry the Ph chromosome, it constitutes the hallmark of CML and is diagnostic of the disease. Approximately 5% of the childhood and 30% of the adult acute lymphocytic leukemias (ALL) also carry the Ph chromosome. The Ph chromosome in CML and ALL results from the same translocation of c-abl to different introns of the bcr gene.

Elimination of cells displaying the Ph karyotype is one indication of remission. An alternate method of assaying for presence of the Ph chromosome is through use of the polymerase chain reaction (PCR) to detect the bcr/abl transcript. Elimination of the bcr/abl transcript upon PCR analysis is indicative of successful elimination of cells leading to CML.

Prior to treatment, the patient (Patient No. 1 in Example 3, below) had relapsed following Allo-BMT and had remained positive for CML markers following a course of Allo-CT accompanied by in vivo treatment with rhIL-2. The patient had not experienced GVHD as a result of the bone marrow transplant or of the Allo-CT/rhIL-2 regimen. Peripheral blood leukocytes (PBL), taken from the same HLA-matched brother who donated cells for the Allo-BMT, were preactivated in vitro by incubation with rhIL-2. The activated donor lymphocytes were administered at a dose between $10^7$ and $10^8$ cells per kilogram body weight. This was followed immediately by a three-day course of rhIL-2 administered in vivo in order to provide a further stimulus to activation following infusion of cells in to the patient.

The patient so treated has not experienced any clinical laboratory signs of GVHD, and has a completely normal bone marrow morphology. Significantly, following the Allo-ACT/rhIL-2 regimen, the PCR test for the presence of the bcr/abl fusion product became negative. As of 28 months post-treatment, the patient displays no evidence for the Ph chromosome, either by cytogenetic or PCR analysis. Additional patients given allogeneic cell therapy are provided in Example 3, below.

In a preferred embodiment for treating human patients with solid tumors, the donor's PBL, unactivated or activated in vitro, are infused into the patient following allogeneic stem cell transplantation. Generally the donor's PBL are infused after the patient has attained at least partial hematopoietic recovery from the stem cell transplant; in many cases, the greater the time interval from stem cell transplantation to administration of donor's PBL, the more lymphocytes can be provided since the risk of uncontrollable GVHD is proportionately less at later times post-transplant. The patient may be administered graded increments of donor's PBL, typically beginning with $10^5$ or $10^6$ T cells/kg and progressing at log increments, e.g., $10^7$, $10^8$, $10^9$ T cells/kg pending no or minimal (controllable) GVHD following the previous infusion. If used, proportionately fewer activated donor lymphocytes are administered compared to the corresponding unactivated donor's PBL. This is because activated lymphocytes, though possibly engendering a heightened anti-tumor effect compared to unactivated lymphocytes, may also put the patient at a somewhat higher risk of GVHD. It is to be noted, however, that if ADL with a limited lifespan are used, then the risk of GVHD is mitigated and larger numbers of ADL may be used. For example, as discussed below, allogeneic lymphocytes may be transduced with a "suicide" gene construct that allows the infused cells to be selectively killed after they have exerted the anti-tumor cell effect in the patient.

For activation of donor's PBL, the cells are incubated in rhIL-2 at a concentration of 60 IU/ml to 12,000 IU/ml, preferably at 600 IU/ml to 8,000 IU/ml, and most preferably at 6,000 IU/ml. It will be evident that these concentrations may be varied to conform to particular incubation media, to different lots and preparations of rhIL-2, and to other routine variations in clinical and laboratory procedures. For example, if the T-cell activator comprises monoclonal antibodies such as anti-CD3 and/or anti-CD28 used in conjunction with rhIL-2, then a correspondingly lower concentration of rhIL-2 may be required. T-cell activators other than IL-2 may be employed in the present procedures, so long as the donor's PBL are appropriately activated. Such alternative T-cell activators can include, without limitation, interleukin-1 (IL-1), interleukin-4 (IL-4), interleukin-5 (IL-5), interleukin 6 (IL-6), interleukin-7 (IL-7), interleukin-12 (IL-12), interleukin-13 (IL-13), interleukin-15 (IL-15), interferon-alpha (IFNα), interferon-gamma (IFNγ), tumor necrosis factors such as TNFα, anti-CD3 antibodies including antigen-binding fragments thereof (anti-CD3), anti-CD28 antibodies including antigen-binding fragments thereof (anti-CD28), phytohemagglutinin, concanavalin-A and phorbol esters.

The donor's PBL are incubated in the T-cell activator until a sufficient level of activation is achieved. For example, the cells may be incubated in T-cell activator such as rhIL-2 for 2 to 14 days, preferably for 4 or 5 days. The length of incubation can be varied to accommodate routine variations in temperature, media formulations, normal variations in PBL responsiveness, use of additional cytokines required to optimize cell growth and activation, and other routine variables, provided that the PBL attain an appropriate state of activation. For example, if relatively large numbers of cells are desired for infusion into the patient, then a correspondingly lengthened incubation time may be required. Various laboratory tests may be used to determine an appropriate end-point for the in vitro activation period. These could include fluorescence-activated cell sorting (FACS) to detect various relevant T-cell phenotypes, and measurement of cytotoxic T lymphocyte precursor activity (CTLp).

To diminish or eliminate the possibility of GVHD, allogeneic donor lymphocytes that are lifespan-limited may be used. For example, donor lymphocytes may be transduced with a susceptibility factor, or "suicide gene," that makes the lymphocytes susceptible to a chemotherapeutic agent. See, e.g., Tiberghien, *J. Leukocyte Biol.* 56: 203–09 (1994). In one embodiment, thymidine kinase from herpes simplex virus (HS-tk) is employed as the suicide gene. Cells expressing HS-tk are sensitive to killing by exposure to acyclovir or ganciclovir. The HS-tk gene may be transferred into T cells via a retroviral vector containing appropriate promoters, selectable markers and/or other flanking elements. Tiberghien et at., *Blood* 84: 1333–41 (1994); Mavilio et al., *Blood* 83: 1988–97 (1994). Following infusion into the patient, such lymphocytes can be selectively killed, after an anti-tumor effect has been engendered but before onset of severe GVHD. Other methods for limiting the lifespan of the infused allogeneic lymphocytes can include without limitation irradiation, photosensitization and use of anti-lymphocyte antibodies.

The exact number of allogeneic lymphocytes infused may depend on availability and on the patient's previously identified risk factors for GVHD. For example, the patient can be started with $10^5$ cells/kg, with escalation by one (1) log increment every 1–4 weeks if no GBHD develops following the previous administration. To allow for continued activation of the allogeneic lymphocytes after infusion into the patient, T-cell activator such as IL-2 can be administered to the patient by subcutaneous injection or any other method appropriate for routine drug delivery. This in vivo administration of T-cell activator is preferably initiated on the same day as infusion of the allogeneic lymphocytes, or can be initiated at any time up to about 7 days after infusion. The in vivo administered T-cell activator can be given over a time course of 1 to 14 days, preferably over a time course of 2 to 7 days, more preferably over a time course of 2 to 4 days, and most preferably for 3 days. In a preferred embodiment, rhIL-2 is infused into the patient for three days at a concentration of $10^6$ to $10^7$, preferably $6 \times 10^6$, $IU/m^2$ of body surface area. The time course and concentrations can be varied to conform with clinical indications such as propensity for GVHD or ability of the patient to tolerate the chosen T-cell activator.

Following the Allo-CT and/or Allo-ACT treatment and, if desired, in vivo treatment with T-cell activator, the patient is monitored for signs and symptoms of GVHD and, where appropriate, for levels of residual malignant cells. Monitoring for levels of residual malignant cells can involve clinical monitoring of the patient for physical symptoms of relapse. Preferably, the monitoring involves evaluation of diagnostic criteria allowing detection of malignant cells prior to manifestation of physical symptoms. For example, cytogenetic studies may be performed in which macroscopic chromosome morphology is examined. Alternatively, the monitoring can include the use of molecular probes to detect, for example, aberrant nucleic acid sequences characteristic of the malignant cells. In the case of CML, the patient can be monitored for evidence of the Ph chromosome as revealed by cytogenetic screening or as revealed by PCR analysis of the bcr/abl transcript in preparations of nucleic acid taken from the peripheral circulation. Other disease-specific markers can be equally useful, such as the alpha-RAR marker for AML-M3 as well as a variety of markers developed for solid tumors of varied origin. Disappearance of the selected markers is an indication that the patient has entered remission as a result of the Allo-CT or Allo-ACT treatment regimen.

In the absence of disease-specific markers, other markers can provided equally useful information about the status of host-derived vs. donor-derived cells. For example, the presence or absence of sex-chromosome-specific markers in the host's circulation can be used to monitor female-to-male or male-to-female host/donor combinations. Likewise, the presence or absence of host-specific bands following VNTR (variable nuclear tandem repeat) searching is equally indicative of the effectiveness of cell therapy.

The invention will be further understood with reference to the following illustrative embodiments, which are purely exemplary, and should not be taken as limiting the true scope of the present invention as described in the claims.

EXAMPLE 1

Induction of a Graft-Versus-Tumor Effect in a Murine Model of Mammary Carcinoma

Materials and Methods

Mice

BALB/c ($H-2^d$) and F1(BALB/cXC57Bl/6)($H-2^{d/b}$) mice aged 10–12 weeks, DAB/2 ($H-2^d$) and C57Bl/6 ($H-2^b$) mice aged 7–9 weeks were obtained from Harlan Sprague Dawley, USA, and maintained in a specific-pathogen free animal house at the Hebrew University Hadassah Medical School, according to Israel-specific national laws.

Tumor

4T1 is one of a series of subpopulations isolated from a single, spontaneously arising mammary tumor of a BALB/cfC3H mouse. Dexter et al, *Cancer Res.* 38: 3174–81 (1978). It is maintained by passage in vitro in RPMI 1640 medium containing 10% heat-inactivated Fetal Bovine Serum (FBS) (Grand Island Biological Co., Grand Island, N.Y.), 2 mM glutamine, 100 mg/ml streptomycin, 100 U/ml penicillin and 1% nonessential amino acids. Preparation of cells for injection includes harvesting by 0.25% trypsin in 0.05% EDTA, washing with RPMI 1640 and resuspending in Hank's medium for intradermal (ID) injection into mice in a volume of 0.1 ml. All tissue culture media and reagents were purchased from Biological Industry, Beit Ha'emek, Israel. Cells were kept at 37° C. in a humidified 5% $CO_2$/air incubator.

Measurement of Primary Tumor Growth in vivo

Tumor size was measured once a week in two perpendicular dimensions with a caliper. Tumor size in $cm^3$ was calculated by the formula $(a \times b^2)/2$ where a is the larger and b is the smaller dimension of the tumor.

Flow Cytometric Analysis

A quantity of $5 \times 10^5$ cells was stained directly with the following monoclonal antibodies: Fluorescein-Isothiocyanate (FITC) anti-$H-2K^d$ and R-phycoerythrin (PE) anti $I-A^d$ (Pharmigen, CA, USA). Indirect staining was carried out using rat anti-mouse ICAM-1 (Takei, J. Immunol. 134: 1403–07 (1985)), VCAM-1 (Miyake et al., J. Exp. Med. 173: 599–607 (1991)), CD44 (Trowbridge et al., Immunogenetics 15: 299–312 (1982)) and B7-1 (Razi-Wolf et al., Proc. Natl. Acad. Sci. USA 89: 4210–14 (1992)) antibodies. An FITC-conjugated affinity-purified fragment (Fab)2 of mouse anti-rat IgG, was used as a secondary antibody (Jackson ImmunoResearch Laboratories Inc., PA, USA). All staining procedures were carried out on ice for 30 min., followed by washing with phosphate-buffered saline containing 1% bovine serum albumin and 0.03% sodium azide. Cells were fixed in 1% paraformaldehyde and analyzed by FACScan cytometry using the Lysys II program (Becton Dickinson, Santa Clara USA).

Immunization Protocol

Cultured 4T1 cells ($10^7$) were irradiated (120 Gy) to ensure the absence of proliferating cells from the immunization dose, then injected intradermally (ID) into naive BALB/c mice 3 times in intervals of 7–10 days. Seven to 10 days following the last immunization dose, a challenge of $10^4$ fresh nonirradiated 4T1 cells was given ID. A control group of naive nonimmunized BALB/c mice as inoculated in parallel with $10^4$ fresh 4T1 cells.

Induction of Bone Marrow Chimeras

Female BALB/c mice were exposed to a lethal dose of 9 Gy total body irradiation (TBI) 24 hr before intravenous injection with $10^7$ bone marrow cells derived from male DBA/2 mice. Female F1(BALB/c×C57Bl/6) mice were exposed to a lethal dose of 11 Gy TBI 24 hr before intravenous injection with $10^7$ bone marrow cells derived from male C57Bl/6 mice. TBI was delivered by linear accelerator at an energy of 6 mev. with a dose rate of 1.9 Gy/min. The bone marrow cells were prepared by flushing RPMI 1640 medium through the shafts of the femora and the tibia of the donors with a 25-gauge needle.

Polymerase Chain Reaction (PCR)

PCR was carried out as previously described. Pugatsch et al., *Leukemia Res.* 17: 900–1002 (1993). Briefly, blood samples were lysed in sterile distilled water and centrifuged for 10 sec at 12,000 g in an Eppendorf centrifuge. Supernatants were discarded and 50 ml 0.05M NaOH were added to the cell pellets. Samples were boiled for 10 min. and 6 ml 1M Tris, pH 7.2, were added. Samples were centrifuged for 5 min. at 12000 g, and care was taken to use only the supernatants for the assay. Oligonucleotide primers were chosen according to the published sequence of a y-chromosome-specific gene (Gubbay et al., *Nature* 346: 245–50 (1990)) from position 22–39 for the 5' primer and 342–359 for the 3' primer, respectively. DNA was amplified in a MJR-Mini Cycler in a total volume of 50 ml. Primers were added at a final concentration of 100 pmol and Taq DNA polymerase (Appligene, France) at 1 U/sample. The following program was used: 94° C.,30"; 50° C.,45"; 72° C.,1'; for a total of 35 cycles. Reaction products were visualized on 1.6% agarose gels (Sigma, St. Louis, USA) containing 0.05% ethidium bromide.

Results

Phenotypic Analysis of 4T1 Cell Surface Markers

Phenotypic characterization of 4T1 murine mammary cell surface markers was carried out by using flow cytometry FACS analysis as described above. 4T1 cultured cells express H-$2^d$ class I antigens (93%) as well as adhesion molecules like ICAM, VCAM (64%, 59%, respectively) and the CD44 homing-associated adhesion molecules (76%). 4T1 cells do not express I-A$^d$ class II antigens, or costimulatory molecules like B7-1.

4T1 Tumorigenicity

The ability of H-$2^d$4T1 cells of BALB/c origin to form tumors in H-2 compatible as well as incompatible hosts was tested. Intradermal inoculation of $10^4$ 4T1 cells into syngeneic H-$2^d$ BALB/c mice resulted in a measurable local tumor in 100% of the mice within 21 days. The primary tumor finally led to lung metastases and death of all mice within a median of 39 days (FIG. 1). A delayed appearance of local tumor was observed only in a fraction of the BALB/c hosts (44%) following inoculation of $10^3$ 4T1 cells. Intradermal inoculation of $10^6$ 4T1 cells into congeneic H-$2^d$ DBA/2 mice caused local tumor and death in only 20% of the mice, while a lower cell dose ($10^5$) led to a transient local tumor that regressed 28 days following tumor inoculation. A measurable primary tumor and lung metastases appeared in 84% of semi-allogeneic H-$2^{d/b}$ hosts mice within 38 days following inoculation of $10^4$ 4T1 cells. All H-$2^{d/b}$ hosts with developed tumor died within a median of 50 days (FIG. 1). Inoculation of H-$2^d$ 4T1 cells into allogeneic H-$2^b$ C57Bl/6 mice failed to cause tumor in any of the hosts even at a cell dose of 5×$10^5$. The results show that 4T1 mammary tumor cells bearing H-$2^d$ antigens can be highly tumorigenic in fully major histocompatible and haploidentical H-2 hosts (BALB/c and (BALB/c×C57Bl/6)F1, respectively), weakly tumorigenic in minor histoincompatible hosts (DBA/2) and are non-tumorigenic in major histoincompatible hosts (C57Bl/6).

Immunogenicity of 4T1 Cell

Figure 2:
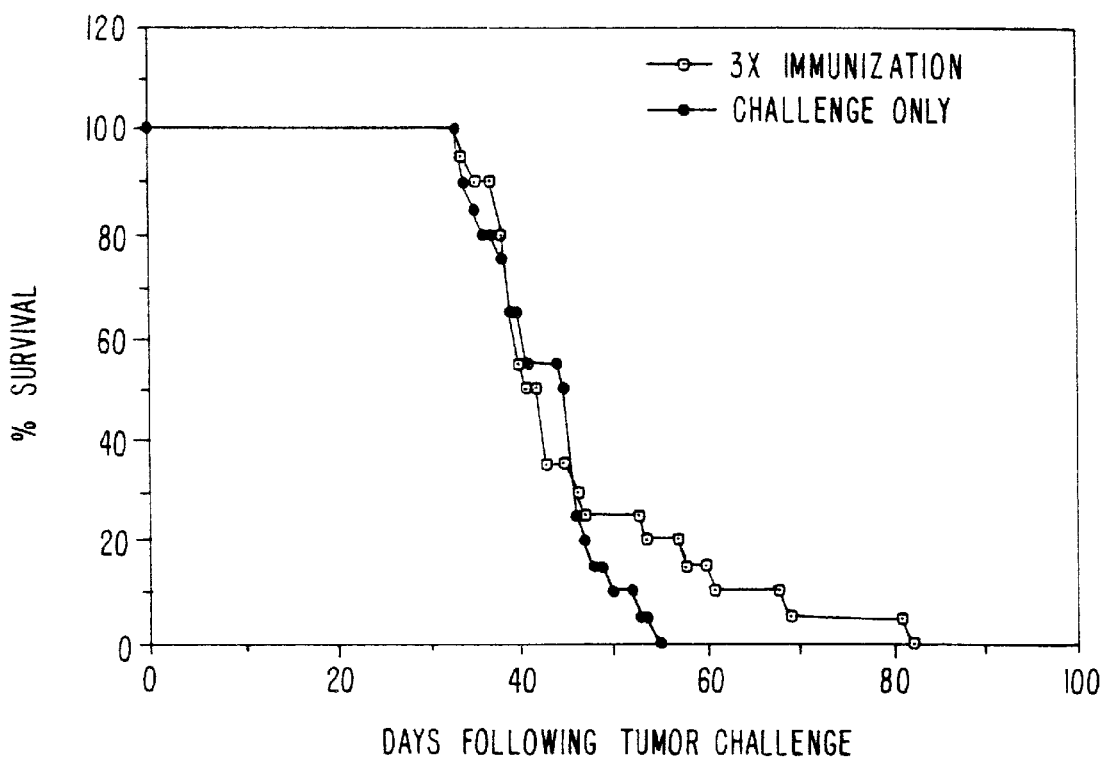
FIG. 2. Percent survival as a function of days following an intradermal challenge dose of ($10^4$) 4T1 cells given to naive BALB/c mice (n=20) or to BALB/c mice (n=20) pre-immunized intradermally 3 times with $10^7$ irradiated 4T1 cells given in intervals of 7–10 days. The challenge dose was injected 7 days after the 3rd immunizing dose.

Irradiated 4T1 cells ($10^7$) were inoculated 3 times in intervals of 7–10 days into syngeneic BABL/c mice before challenging with a fresh tumorigenic dose of $10^4$ 4T1 cells. These multiple injections of irradiated 4T1 cells did not induce immune protection against a challenge of non-irradiated 4T1 tumor cells (FIG. 2). All mice died with a large local primary tumor as well as lung metastases in a median of 42 days following challenge inoculation. Naive BALB/c mice inoculated with a challenge dose only died in a median of 45 days. Inoculation of either a lower dose of irradiated cells or the same cell dose given only once or twice, failed to induce tumor immunity (data not shown).

Induction of BM Chimeras across Minor and Major Histocompatible Antigens

Figure 3:
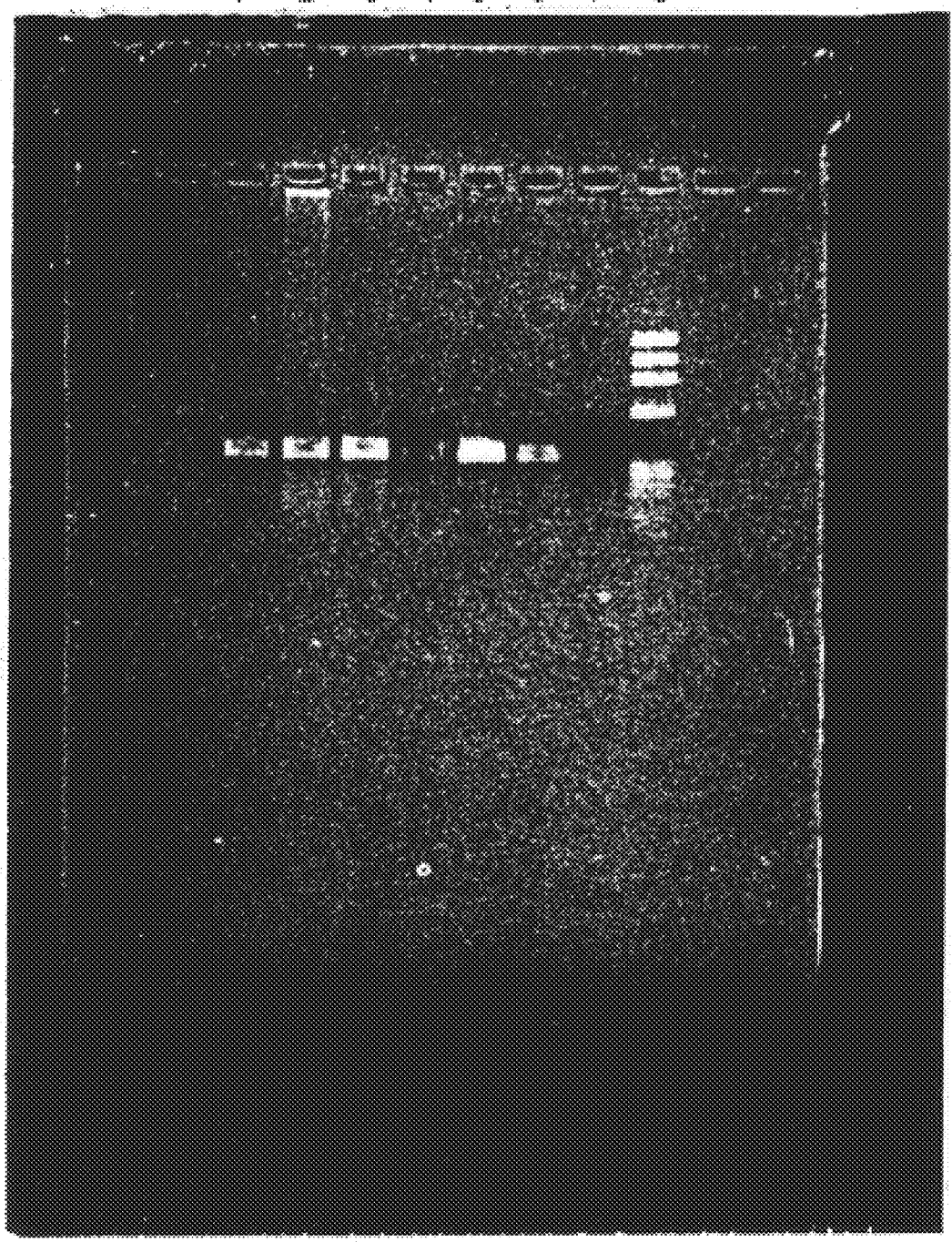
FIG. 3. Detection of y-chromosome by PCR analysis. Peripheral blood samples were taken from female recipient BALB/c mice 1,3,6 and 9 months following hematopoietic reconstitution with male DBA/2 donor cells (Lanes: 1–4, respectively). Lane 5: male positive control direct PCR. Lane 6: positive DNA control. Lane 7: no DNA control. Lane 8: Hae III size markers. The intensity of the signal depends on the number of cells, which was different in each sample.

Recipient BALB/c (H-$2^d$) and (BALB/c×C57Bl/6) F1 (H-$2^{d/b}$) female mice were reconstituted with male-derived minor histoincompatible DBA/2-derived (H-$2^d$) and major histoincompatible C57Bl/6-derived (H-$2^b$) bone marrow cells, respectively, following a lethal does of TBI (data not shown). Induction of hematopoietic chimeras was tested using molecular analysis for detection of male y chromosome sequences in peripheral blood cell samples taken 1, 3, 6 and 9 months following BM reconstitution. Results presented in FIG. 3 show evidence for presence of the y-chromosome marker as early as 1 month following bone marrow cell inoculation and continuation of its dominant presence throughout a period of >280 days in DBA-BALB/c chimeras. A stable hematopoietic chimerism was established with light symptoms of chronic GVHD (fur and slight weight loss) across minor histocompatible antigens and with no GVHD overt symptoms across major histocompatible antigens. Respectively, survival time of 9 DBA-BALB/c chimeras was 261 (median) with a range of 147–341 days and >300 days in 14 C57Bl/6-F1 chimeras.

Tumorigenicity of 4T1 Cells in Hematopoietic Chimeras

Figure 4:
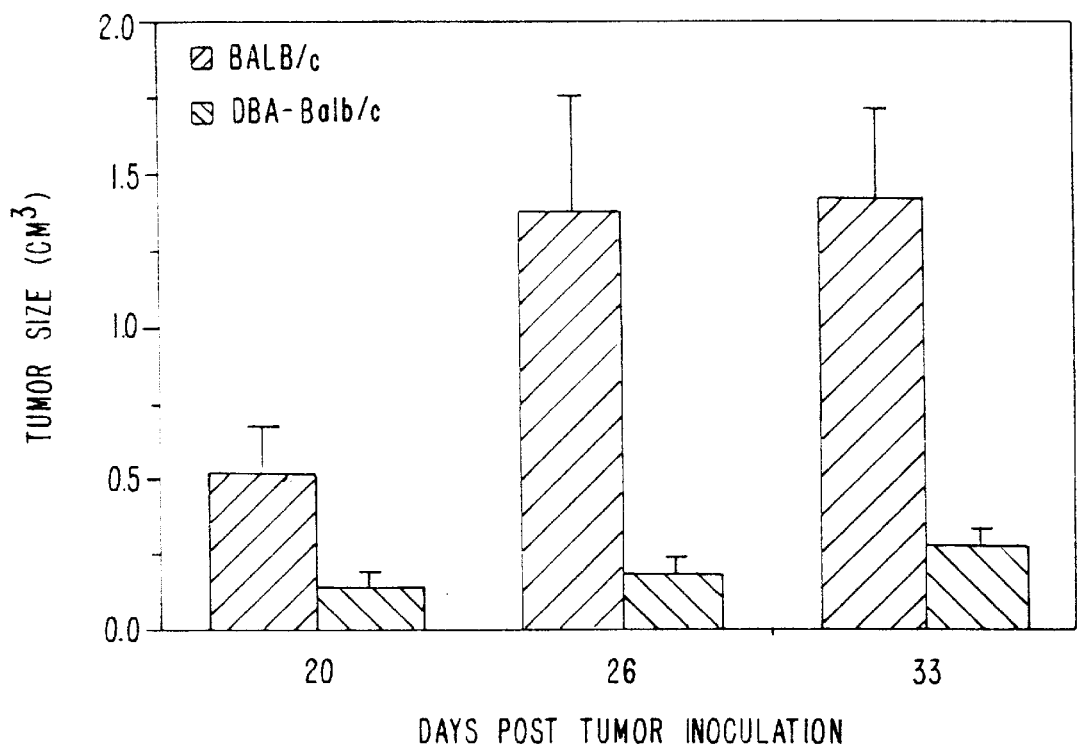
FIG. 4. 4T1 tumor size as function of days following tumor inoculation into 13 naive BALB/c mice and 15 chimeric BALB/c mice reconstituted with DBA/2 hematopoietic cells (DBA—BALB/c). Tumor cells were inoculated into chimeric mice 60–90 days following bone marrow cell reconstitution. Results represent 3 separate experiments.
Figure 5:
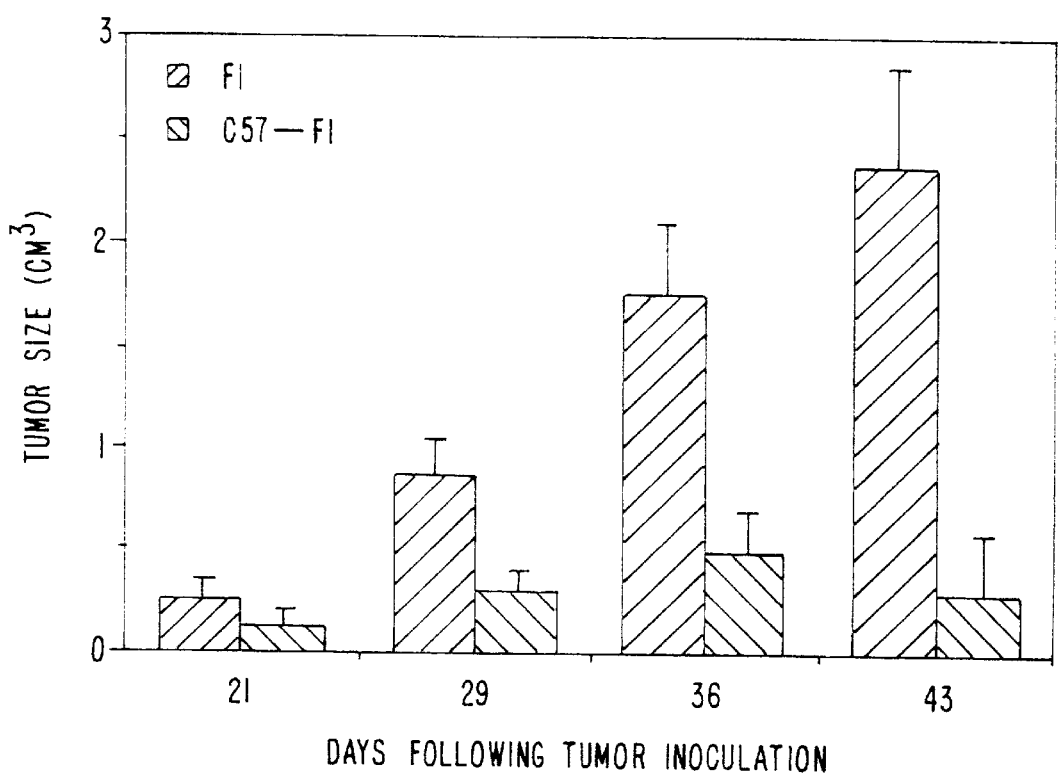
FIG. 5. 4T1 tumor size as function of days following tumor ell inoculation into 18 naive F1 (BALB/cx×C57Bl/6) mice and 11 chimeric F1 mice reconstituted with C57Bl/6 hematopoietic cells (C57—F1). Tumor cells were inoculated into chimeric mice 60–90 days following bone marrow cell reconstitution. Results represent 3 separate experiments.

4T1 tumor cells bearing H-$2^d$ histocompatible antigens of BALB/c origin were inoculated intradermal into naive BALB/c (H-$2^d$) mice and into BALB/c chimeras carrying minor histoincompatible hematopoietic cells of DBA/2(H-$2^d$) origin. Tumor size as a function of days following tumor inoculation is presented in FIG. 4. A measurable local tumor on day 20 was markedly increased with time up to 1.43 cm$^3$ in naive BALB/c mice. A significantly smaller tumor ($p<0.01$) with a limited growth up to 0.27 cm$^3$ was observed in chimeric DBA-BALB/c mice. Inoculation of 4T1 cells into naive F1 (H-$2^{d/b}$) mice and F1 chimeras carrying major histoincompatible hematopoietic cells of C57Bl/6origin, showed a local primary tumor of 0.26 cm$^3$ which was further increased up to 2.40 cm$^3$ in naive F1 mice and was significantly smaller (p<0.05) with limited growth up to 0.31 cm$^3$ in chimeric C57Bl/6—F1 mice (FIG. 5).

EXAMPLE 2

Graft-Versus-Tumor Effects in a Murine Model of Leukemia

1. Procedures

Inbred, 8–12 week old male and female BALB/c, C57Bl/6 (B6) and (BALB/c×B6) F1 (F1) mice were purchased from the Jackson Memorial Laboratory, Bar Harbor Me., USA. Mice were kept in small isolated cages (5 animals in each cage) and fed sterile food and acidic water (pH 3.0) during induction of chimerism. Inoculation of leukemia and post-transplant immunotherapy were carried out in a standard non-isolated animal facility.

BALB/c mice were exposed to a single dose of 10 Gy total body irradiation (TBI) from a gamma 150-A$^{60}$Co source (Atomic Energy of Canada) with a focus to skin distance of 75 cm at a dose rate of 58 cGy/min. Twenty-four hours later, the lethally irradiated mice received 5×10$^6$ T-cell depleted bone marrow cells from B6 donors via the lateral tail vein. Marrow inocula were enriched for stem cells and depleted of immunocompetent T cells by soybean lectin agglutination, according to Reisner et al Reisner et al., Proc. Natl. Acad. Sci. USA 75:2933 (1978), with minor modifications as reported in Schwarz et al., J. Immunol 138:460 (1987).

rhIL-2 was supplied by Dr. C. R. Franks, EuroCetus BV, Amsterdam, The Netherlands, as 1 mg Proleukin (18×10$^6$ International Units=3×10$^6$ Cetus Units). rhIL-2 was initially diluted with water for injection and subsequently rediluted with 5% dextrose.

BCL1 cells were maintained in vivo in BALB/c mice by intravenous passages of 10$^6$–10$^7$ peripheral blood lymphocytes (PBL) obtained from tumor bearing mice. All recipients of BCL1 cells developed splenomegaly and marked lymphocytosis in the blood at the time they were sacrificed to be used as donors for BCL1 cells in experimental mice. Slavin et al., Cancer Res. 41:4162 (1981). PBL counts of all experimental groups were carried out weekly. Onset of leukemia was defined as PBL counts exceeding 20,000/mm$^3$. At the peak of disease PBL counts usually reached >100,000/mm$^3$. Survival of BCL1 recipients was monitored daily.

Chimerism (i.e., presence of non-self, i.e, donor, hematopoietic cells in a recipient) was determined 4–9 weeks after BMT from the peripheral blood or spleen cells, as previously described. Lapidot et al., Blood 73:2025 (1989). Chimerism was reconfirmed by assaying PBL using an in vitro complement-dependent microcytotoxicity assay, with specific alloantisera (BALB/c anti-B6 and B6 anti-BALB/c) and rabbit-complement, prior to inoculation with BCL1 cells. The percentage of host- or donor-type cells was determined by the trypan blue dye exclusion assay. The specific alloantisera were prepared by cross-immunizing mice with a full-thickness skin allograft followed by 6 intraperitoneal injections of 30–50×10$^6$ donor-type spleen cells given 1–2 weeks apart. Mice were bled and sera were stored at –70° C. Chimerism was tested by typing each lymphocyte sample with both antisera: lymphocytes obtained from F1 recipients were lysed 100% by both BALB/c anti-B6 and B6 anti-BALB/c antisera, whereas lymphocytes obtained from B6-BALB/c chimeras were lysed 100% only by BALB/c anti-B6 antiserum; B6 anti-BALB/c antiserum was used to confirm elimination of host cells. The net percentage of chimerism was calculated as follows: percentage of cells lysed following treatment with BALB/c anti-B6 antisera (average of duplicate assays) minus cells lysed following treatment with B6 anti-BALB/c antisera minus cells lysed with complement alone.

2. Results

Evidence for Chimerism in BALB/c Mice Transplanted with T-cell Depleted B6 Bone Marrow As described above, BALB/c mice were lethally irradiated and reconstituted with T-cell depleted B6 bone marrow cells. Chimerism was confirmed by assaying PBL shortly after transplantation and again three months later, immediately prior to inoculation with BCL1 cells. All mice were found to be chimeric. Percentages of donor type cells in the blood ranged between 74 and 100%. None of the chimeras showed any clinical evidence of GVHD and the body weight of chimeras was comparable to the body weight of normal controls (data not shown).

Resistance of Chimeras to BCL1

Figure 6:
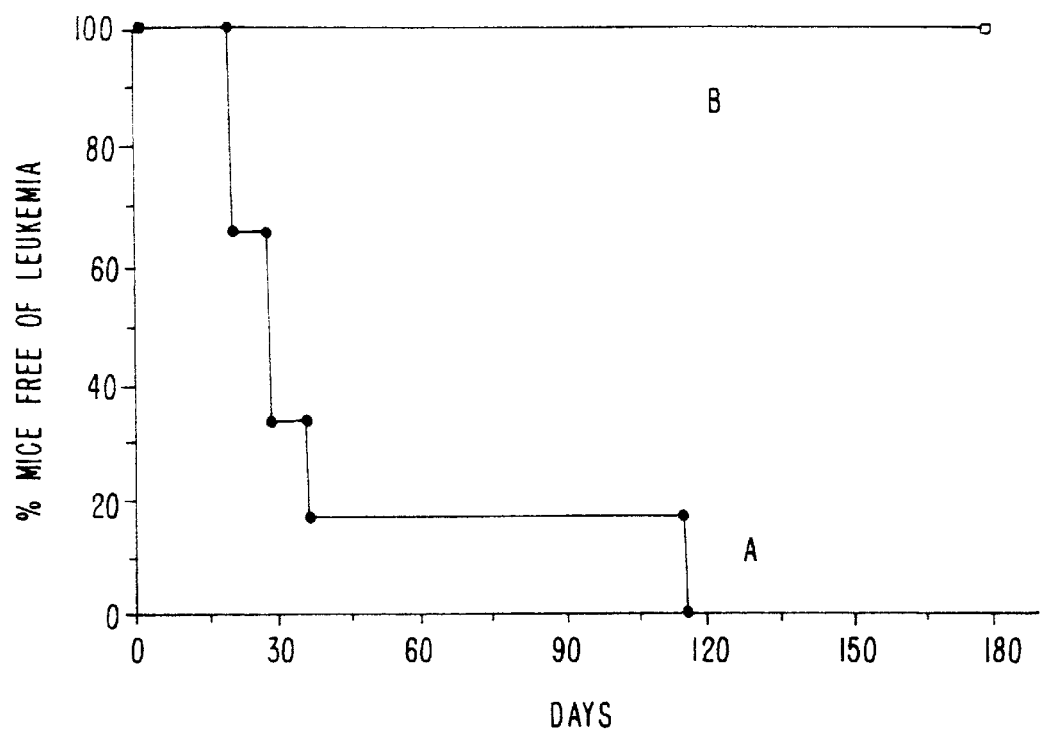
FIG. 6. Development of leukemia in normal BALB/c control mice (group A, n=10) and in B6→BALB/c chimeric mice (group B, n=12) inoculated intravenously with $10^6$ BCL1 cells.

Normal BALB/c mice and B6-BALB/c chimeras were injected intravenously with 10$^6$ BCL1 cells. All normal BALB/c mice developed leukemia, the majority within less than 40 days (median 21 days), and died, whereas all 10 chimeras tested survived with no evidence of disease for >6 months (FIG. 6). A total dose of 10$^2$ BCL1 cells is sufficient to cause 100% death from leukemia in normal BALB/c recipients (data not shown). Slavin et al. Cancer Res. 41:4162 (1989).

Elimination of Clonogenic BCL1 Cells in B6→BALB/c Chimeras with No GVHD

Figure 7:
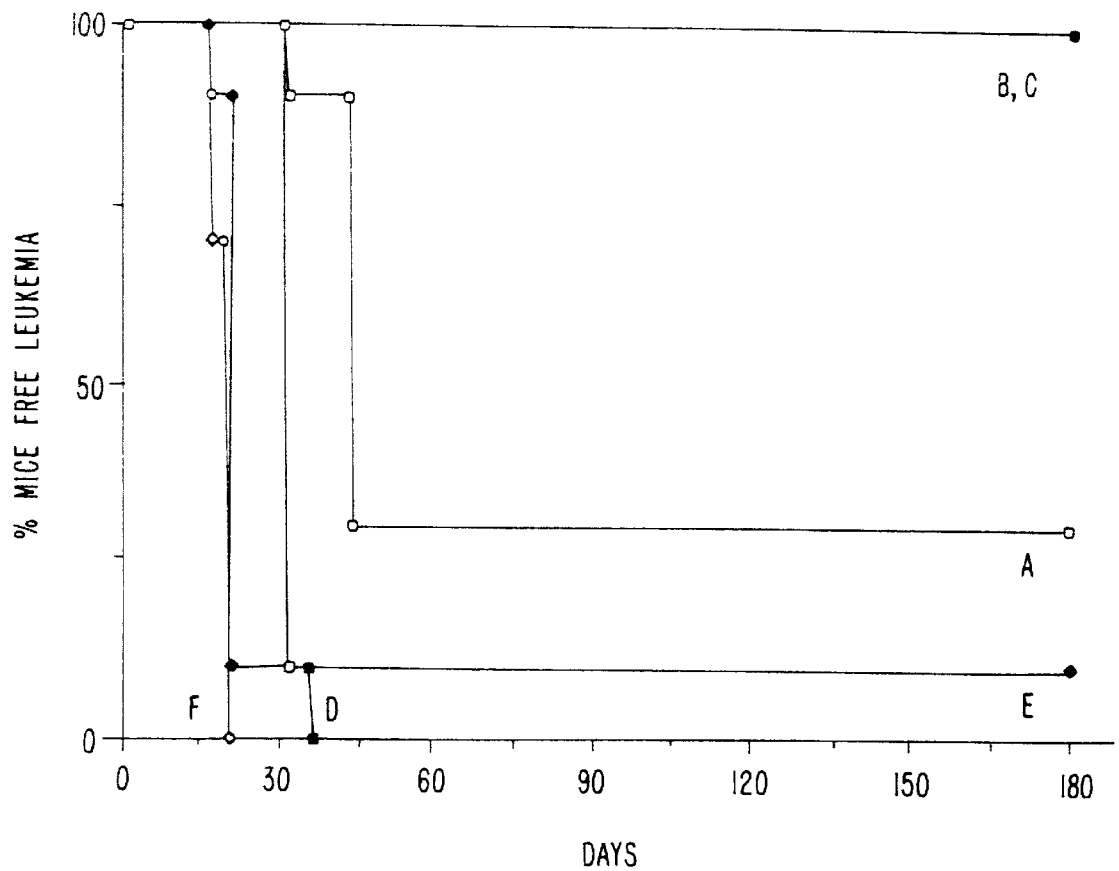
FIG. 7. Time intervals needed for effective GVL effects: development of leukemia in secondary adoptive recipient BALB/c mice after receiving $10^5$ spleen cells obtained from B6→BALB/c chimeras inoculated with $10^6$ BCL1 cells at 7 days (group A), 14 days (group B) and 21 days (group C) prior to adoptive transfer; and from normal BALB/c mice inoculated with $10^6$ BCL1 cells: 7 days (group D), 14 days (group E) and 21 days (group F) prior to adoptive transfer. Each group consisted of 10 mice.

None of the B6-BALB/c chimeras displayed any clinical evidence of GVHD. In order to follow the fate of large numbers of clonogenic BCL1 cells given to the B6→→BALB/c chimeras, adoptive transfer experiments were carried out. 10$^5$ spleen cells (prepared from a pool of 3 chimeras) were transferred to 10 secondary naive BALB/c mice 7, 14, and 21 days post-inoculation with 10$^6$ BCL1 cells (FIG. 7). With the exception of a single mouse (1/30), all adoptive recipients of control spleen cells, obtained from normal mice 1, 2, and 3 weeks following inoculation with BCL1 cells developed leukemia within 37 days and died. Seven of 10 secondary recipients of cells obtained from chimeras inoculated 7 days prior to cell transfer developed leukemia within 44 days. In contrast, none of the adoptive recipients of spleen cells obtained from B6→BALB/c chimeras at 14 and 21 days post-inoculation with BCL1 developed leukemia when monitored for more than 6 months. The data suggest that a period of at least 14 days is required for complete eradication and/or inactivation of 10$^6$ BCL1 cells, whereas at 7 days eradication of leukemic cells is still incomplete.

Figure 8:
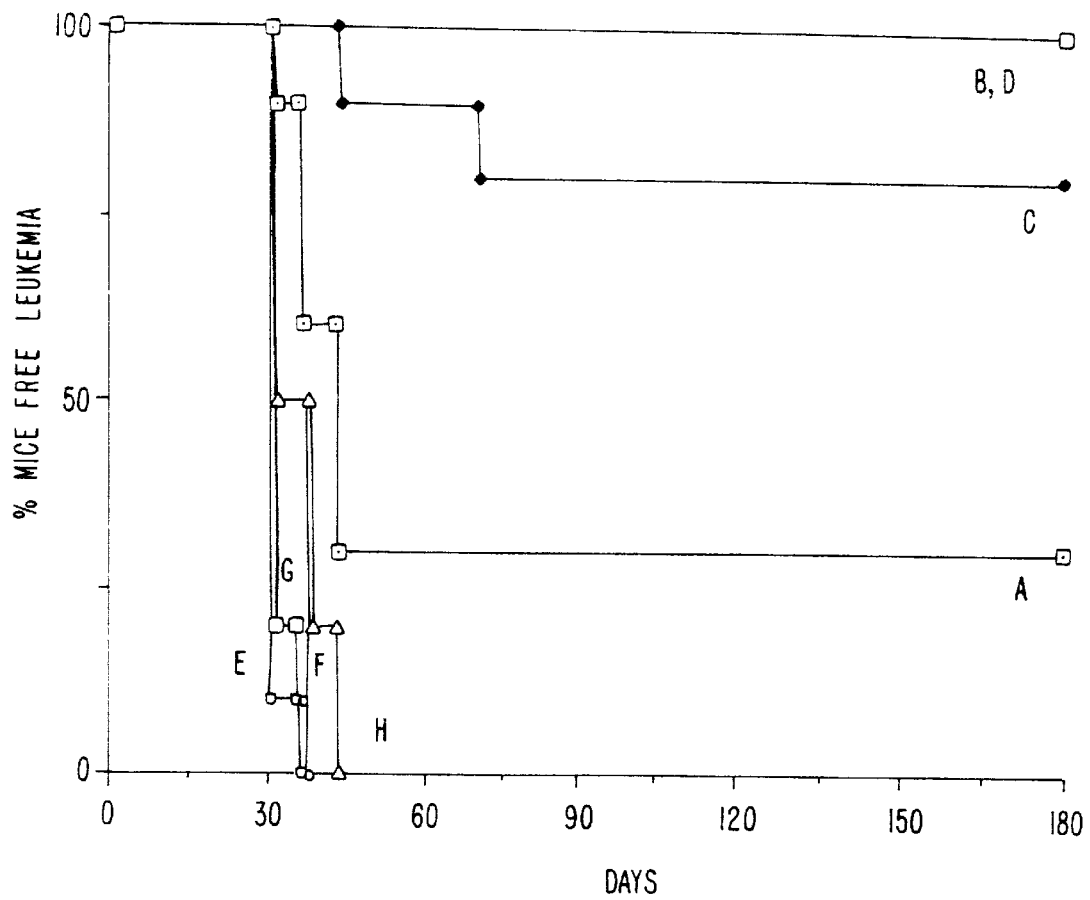
FIG. 8. Amplification of GVL effects by allogeneic spleen cells and rhIL-2: development of leukemia in secondary adoptive recipient BALB/c mice after receiving $10^5$ spleen cells obtained from B6→BALB/c chimeras or normal BALB/c mice 7 days post-inoculation with $10^6$ BCL1 cells. Group A: untreated chimeras: group B: chimeras injected with rhIL-2; group C: chimeras infused with spleen cells; group D: chimeras infused with spleen cells and with rhIL-2; group E: normal BALB/c controls without further treatment; group F: normal BALB/c controls injected with rhIL-2; group G: normal BALB/c controls infused with spleen cells; group H: normal BALB/c controls infused with spleen cells and with rhIL-2. Each experimental group consisted of 10 mice.

Amplification of GVL Effects by Immunocompetent Allogeneic Spleen Cells and rhIL-2 Therapy in Chimeras Inoculated with BCL1 Cells Twenty-four normal BALB/c mice and 24 well established B6-BALB/c chimeras were injected with 10$^6$ BCL1 cells. Injected chimeras were divided into 4 groups. (A) B6→BALB/c chimeras serving as controls with no additional therapy; (B) B6→BALB/c chimeras receiving rhIL-2 (10,000 IU ×3/day intraperitoneally for 5 days) starting one day following inoculation with leukemic cells; (C) B6→BALB/c chimeras receiving $10^7$ normal immunocompetent B6 spleen cells; (D) B6→BALB/c chimeras receiving both $10^7$ normal B6 spleen cells and rhIL-2. For comparison, several controls were included: (E) a control group of normal BALB/c mice inoculated with $10^6$ BCL1 cells with no additional therapy; normal BALB/c mice inoculated with $10^6$ BCL1 cells received either rhIL-2 (F) or allogeneic spleen cells (G) or both (H). Seven days later all mice were sacrificed and their spleen cells were used for adoptive transfer experiments to assess the presence of clonogenic BCL1 cells. Secondary BALB/c recipients (5 in each group) received $10^5$ spleen cells obtained from a pool of 3 control BALB/c mice or from 3 B6→BALB/c chimeras of each experimental group. Matching results were obtained when the experiment was duplicated with the remaining three mice of each group. The data were therefore pooled and each experimental group shown in FIG. 8 consists of 10 mice.

All secondary BALB/c recipients receiving spleen cells obtained from normal BALB/c mice (E) developed leukemia within 32–37 days. Seventy percent of secondary recipients receiving spleen cells obtained from B6→BALB/c chimeras (group A) did not develop leukemia for >6 months, whereas in the 30% that did develop leukemia, the onset of disease was delayed (onset within 44–52 days). B6→BALB/c chimeras treated with rhIL-2 (B), allogeneic immunocompetent donor-type splenocytes (C) or the combination treatment of both (D) displayed marked resistance against leukemia, with no evidence of disease for >6 months in all secondary recipients of spleen cells obtained from groups B and D and with delayed onset of leukemia in only 20% of mice receiving spleen cells from group C. No anti-leukemia effects were detected in normal control BALB/c mice treated with rhIL-2, allogeneic splenocytes or both (F, G, and H, respectively).

EXAMPLE 3

Clinical Results

I. Breast Cancer

A 40 year old female patient presented who had developed an upper medial quadrant mass in the left breast at the age of 37. Physical examination revealed an undefined mass at that region and a 4×3 cm mass in the left axilla. Excisional biopsy was taken from the breast mass and the pathological examination revealed a grade III multifocal infiltrating ductal carcinoma with three masses of 3×2×2, 1.5×1×1 and 1×1×1 cm in size. In addition, there was tumor invasion to the lymphatic vessels with a positive surgical margin. The patient was treated with 7 cycles of CAF (Cyclophosphamide, Adriamycin and 5 Fluro-uracil). Chemotherapy was followed by left upper quadrantectomy and axillary lymph node dissection. The pathological report from this specimen revealed three residual foci of infiltrating ductal carcinoma of 1×1×1, 1×1×1.5 and 0.5×0.5×0.5 cm in size. Three out of 17 nodes were involved with cancer. The patient completed 56 Gy breast irradiation followed by a 14 Gy boost dose to the tumor area using 12 MeV electron beam irradiation.

Twenty three months later a 1.5 cm mass was noted in the medial aspect of the quadrantectomy scar adherent to the chest wall. FNA aspiration was performed and cytological analysis revealed malignant cells which were consistent with breast cancer. Blood count at that time showed Hgb of 7.5 g % and WBC of $1.3\times10^9$/L. Bone marrow biopsy was performed and the diagnosis was compatible with AML-M2. Analysis of the phenotype of the blast cells by fluorescence activated cell sorter showed HLA-DR 76%, CD34 65%, CD33 66%, CD13 56%, CD15 41%, CD11B 40% and CD11C 80%. Systemic evaluation included whole body CT scan, abdominal ultrasound, liver scan, bone scan, CA-15-3 and CEA; all were within the normal range. The patient was treated with one cycle of amscarine and high dose cytosar with subsequent disappearance of blast cells in bone marrow. A slight decrease in the size of the chest wall mass was noted.

Four months following the diagnosis of AML, the patient underwent a T cell depleted allogeneic stem cell transplantation from a full HLA A, B, C, DR and DRB1-matched MLR non-responsive brother. The conditioning protocol included pretransplant immunosuppression with anti-thymocyte globulin (Fresenius) 10 mg/kg for 4 consecutive days and subsequent administration of busulfan 4 mg/kg/day×4, thiotepa 10 mg/kg/day×1, cytoxan 50 mg/kg/day×4 and intrathecal ARA-C for CNS disease prophylaxis. T cell depletion was accomplished by adding monoclonal rat anti-human lymphocyte (CDw52) antibody (Campath-1G, provided by Dr. G. Hale, Oxford University, UK) at 0.3 ug/$10^6$ nucleated cells to the bag containing the marrow cells as previously described (Naparstek et al., *Exp. Hematol.* 17: 723 (abstr.) (1989)). Engraftment (ANC>$0.5\times10^9$/L, PLT>$25\times10^9$/L) was documented on the 21st day following transplantation. Following transplantation the cytogenetic studies revealed full reconstitution with donor-derived cells in the blood.

Ten weeks following the transplantation there were no clinical signs of GVHD; hence, the patient was treated with allogeneic cell-mediated immunotherapy (allo-CT) consisting of donor blood lymphocyte infusion at a cell dose equivalent to $1\times10^5$ T cells/kg. Four weeks later a transient impairment of liver function tests (GGTP 712, ALT 301, and AST 258 Units) was observed. No other clinical findings indicative of GVHD were noted. Twenty weeks post transplant, a higher dose of donor blood lymphocytes consisting of $0.6\times10^6$ T cells/kg was given. At greater than 8 months post-transplant, the patient is event free with no evidence of either breast cancer or AML. No evidence of acute or chronic graft vs host disease (GVHD) developed although the patient received no anti-GVHD prophylaxis.

The present inventor is not aware of any cases in which a patient with such an aggressive recurrent breast cancer went into stable complete response after receiving only "suboptimal" chemotherapy as was used in this patient.

II. Hematologic Malignancies

Patient No. 1. A 17 year-old man with CML in accelerated phase was admitted to Hadassah University Hospital Department of Bone Marrow Transplantation for allogeneic BMT. The patient had an HLA-A, B, DR, DRB1 matched brother non-reactive in bilateral mixed lymphocyte culture for allogeneic BMT. Pre-transplant cytogenetic analysis of the patient disclosed 100% $Ph^1$ positivity in bone marrow spontaneous metaphases with three different malignant translocation clones: 35% 46XY t(9:22); 35% 46XY t (9:22) add (15) (q26); 30% 46XY t(9:22 add (2) (q37). Additionally, the patient was classified as 100% positive for the bcr/abl fusion product, as detected by PCR in a peripheral blood sample. Pre-transplant conditioning included cyclophosphamide (60 mg/Kg×2 days) and total body irradiation (200 cGy daily×6 days).

On Jul. 21, 1993, he was transplanted with $2.5\times10^8$ viable nucleated cells/kg (non-T-cell depleted) from his compatible brother. He was treated with cyclosporin A (starting day −1) and methotrexate (days 1, 3, 6 and 11) as anti-GVHD prophylaxis as previously described. Goldman, Leuk. and Lymph. 3: 159–64 (1990). The graftment was normal with white blood cell (WBC) count >1×10$^9$/L on day +26, neutrophil count >0.5×10$^9$/L on day +25 and platelet count >25×10$^9$/L on day +25. He was discharged 24 days post BMT in very good general condition with no signs of GVHD. At one month post BMT, PCR disclosed no bcr/abl fusion product. Cyclosporin A was tapered off and discontinued 3 months post BMT. A month later, at 4 months post BMT, the PCR converted to bcr/abl positivity and marrow cytogenetic analysis revealed 100% Ph+ with clonal selection. Marrow morphology was compatible with chronic phase CML. No significant increase in peripheral blood counts was noticed.

In an attempt to reinduce remission he was treated with allogeneic cell-mediated immunotherapy (Allo-CT) using the compatible brother's peripheral blood lymphocytes (PBL) (8.9×10$^7$ cells infused/kg). Two weeks later, in the absence of any sign of GVHD, the patient was given another infusion of PBL (5×10$^7$ cells/kg) with in vivo rhIL-2 (3×10$^6$ IU/M$^2$) given subcutaneously for 3 consecutive days on an outpatient basis. No signs of GVHD developed. There was a transient decline in the WBC counts from 14.7×10$^9$/L to 6.2×10$^7$/L with no change in the hemoglobin and platelet counts. The PCR for the bcr/abl fusion product remained positive. With continued evidence of malignant cells following BMT and Allo-CT, the patient's prognosis was very poor absent additional therapeutic measures.

In an attempt to escalate the therapeutic regimen, PBL from the compatible brother were precultured in RPMI medium (Beit HaemeK, Israel) supplemented with 5% inactivated autologous AB serum and further supplemented with 6,000 IU/ml of rhIL-2. The PBL were maintained in this medium for 4 days in a humidified 5% CO$_2$ in air incubator, at a concentration of 2.5×10$^6$ cells/ml. After 4 days incubation of an initial cell dose of 17×10$^8$ viable cells, a total of 28×10$^8$ ADL were harvested.

In January 1994, the patient received 3.7×10$^7$ allogeneic ADL/kg, together with 3 days administration of subcutaneous rhIL-2 (3×10$^6$ IU/m2), beginning on the same day as the ADL administration, for further in vivo activation of the allogeneic ADL. The WBC dropped from 11.3×10$^9$/L to 1.3×10$^9$/L. Hemoglobin dropped from 11.5 g % to 8.3 g % and the platelet count dropped from 346×10$^9$/L to 23×10$^9$/L. PCR became negative for the bcr/abl fusion product. Bone marrow cytogenetic analysis detected 100% normal male karyotype in all spontaneous metaphases. Bone marrow morphology was completely normal and there were no clinical laboratory signs of GVHD. Blood counts improved gradually with no further therapy. At 2 months following Allo-ACT, at the time the WBC count was 2.8×10$^9$/L, platelet 78×10$^9$/L and hemoglobin 10.2 g %, the patient developed disseminated herpes zoster with abnormal liver function tests including bilirubin 17 (normal range 2.5–17) micromol/L, AST 444 (normal range 7–40) units, ALT 561 (normal range 6–53) units, GTP 346 (normal range 60–170) units. The patient is more than 28 months post Allo-ACT with no evidence of the Ph+ clone (by both cytogenetics and PCR analysis) and with no signs of severe GVHD and good general condition.

Patient No. 2. A five-year-old boy was diagnosed with calla-positive acute lymphocytic leukemia (ALL) in 1988. Allogeneic BMT was performed in Barcelona, Spain on Jan. 8, 1990. At the time of BMT, the patient was in a second complete remission. The conditioning regimen consisted of cyclophosphamide, 60 mg/kg on two consecutive days, plus fractionated total body irradiation (TBI), 200 cGY×6 (a total of 1200 cGY). The donor bone marrow was from a fully matched brother, and was given without T-cell depletion. The patient was given standard post-transplant anti-GVHD prophylaxis with cyclosporin A. Following BMT, Grade I GVHD developed. Overt hematologic and cytogenetic relapse was diagnosed one month later with T(2;3), (Q37;P14), DEL(13) (Q?), DEL (20) (Q11) clones.

The patient received post-transplant Allo-CT consisting of the donor's PBL at an equivalent dose of 1.4×10$^7$ T cells/kg given on Oct. 8, 1991, followed on Nov. 3, 1991 by 3.5×10$^8$ T cells/kg with concomitant administration of rhIL-2 subcutaneously (6×10$^6$ IU/m$^2$) for 3 consecutive days starting on the day of cell infusion. Subsequently, in December of 1991, the patient received 3×10$^8$ ADL/kg prepared by treating donor PBL in vitro with 6,000 IU/ml of rhIL-2 for 4 days. Five days later, the patient developed cutaneous GVHD grade III which responded over the course of one month to corticosteroid therapy. Following the Allo-ACT+in vivo T-cell activator regimen, the patient entered a complete remission, documented by a normal cytogenetic pattern observed in all metaphases investigated. Chronic GVHD of the skin has persisted, and the patient remains in complete remission over 53 months post Allo-ACT.

Patient No. 3. A nine-year-old girl was initially diagnosed in September 1990 with adult-type CML, 100% Philadelphia chromosome-positive cells. She underwent allogeneic BMT on Feb. 21, 1991, in Seattle, while in Chronic Phase. Conditioning consisted of cyclophosphamide, 60 mg/kg, on two consecutive days, followed by fractionated TBI, 200 cGY×6 (total dose of 1200 cGY). A full HLA AB DR-matched MLR non-reactive brother was the donor, and the donor's cells were not T-cell depleted. The patient received standard anti-GVHD prophylaxis with cyclosporin A, and developed no GVHD. Nine months following BMT, the patient had overt hematologic and cytogenetic relapse with 100% of the observed metaphases revealing the Philadelphia chromosome.

The patient received PBL from the same donor at an equivalent dose of 5×10$^6$ T cells/kg given on Dec. 3, 1991. The donor was less than three years old and, therefore, full pheresis was not technically feasible. The patient received a total dose of donor PBL equivalent to 10$^7$ T cells/kg on Jan. 15, 1992, with concomitant administration of rhIL-2 subcutaneously (6×10$^6$ IU/m$^2$) for 3 consecutive days starting on the day of cell infusion. Subsequently, in February of 1992, the patient received ADL at an equivalent dose of 10$^7$ cells/kg. In March of 1992, a second dose of 10$^7$ ADL/kg was administered with concomitant administration of rhIL-2 subcutaneously (6×10$^6$ IU/m$^2$) for 3 consecutive days starting on the day of cell infusion. The ADL were prepared by treating donor PBL in vitro with 6,000 IU/ml of rhIL-2 for 4 days.

The patient responded hematologically; however, a reverse transcriptase PCR assay (RT-PCR) indicated the presence of residual Philadelphia chromosome-positive cells. Following treatment with alpha interferon (Roferon A), all cytogenetic abnormalities disappeared as evidenced by a negative RT-PCR assay for the bcr/abl fusion product. The patient showed no evidence of GVHD throughout the treatment. The patient is doing very well over 51 months post Allo-ACT; she is hematologically normal with no abnormal karyotypes and is consistently negative by RT-PCR for the bcr/abl fusion product. She is in excellent clinical condition with no signs of chronic GVHD.

Patient No. 4. A three year old girl was diagnosed with adult-type, Philadelphia chromosome-positive CML in November of 1990. The patient was conditioned for allogeneic BMT with busulfan, 16 mg/kg over four consecutive days and with cytoxan, 200 mg/kg over four consecutive days. Cells for allogeneic BMT were taken from a fully matched minor brother (one year old). The BMT was performed, without T cell-depletion, on May 2, 1991, with standard anti-GVHD prophylaxis using cyclosporin A. The patient had an uneventful outcome following BMT, with no GVHD. At 8 months post-BMT, the patient developed overt hematologic and cytogenetic relapse.

Cell therapy consisted of donor PBL from the BMT donor at an equivalent dose of $5 \times 10^6$ T cells/kg administered in February 1992. A similar dose of donor PBL was administered in March of 1992, with concomitant administration of rhIL-2 subcutaneously ($6 \times 10^6$ IU/m$^2$) for 3 consecutive days starting on the day of cell infusion. In April of 1992, the patient received ADL from the BMT donor at an equivalent dose of $5 \times 10^6$ T cells/kg. In July of 1992, the patient received ADL from the BMT donor at an equivalent dose of $3 \times 10^6$ T cells/kg with concomitant administration of rhIL-2 subcutaneously ($6 \times 10^6$ IU/m$^2$) for 3 consecutive days starting on the day of cell infusion.

No signs of GVHD developed and, perhaps consequently, the patient showed progressive disease despite the cellular immunotherapy. Further treatment with Roferon A failed to induce cytogenetic remission. The patient underwent a second allogeneic BMT with no T cell-depletion in September of 1994, but died due to progressive disease.

Patient No. 5. A two year old girl was diagnosed in August of 1992 with myelodysplastic syndrome (MDS) refractory anemia, with excess blasts displaying a clonal t(9:11) translocation, evidence of transition to leukemia. Allogeneic BMT from a fully HLA A B DR DRB1-matched and MLR non-responsive brother was carried out on Feb. 10, 1993. Conditioning consisted of busulfan, 16 mg/kg given over four consecutive days, thiotepa, 10 mg/kg given over two consecutive days, and cytoxan, 16 mg/kg given over two consecutive days. The allogeneic BMT was non-T-cell depleted, and the patient had a non-eventful outcome with no signs of GVHD following standard anti-GVHD prophylaxis with cyclosporin A. The patient went into full relapse with the same clonogenic leukemia at five months following BMT.

In August of 1993, the patient was treated with donor PBL from the BMT donor at an equivalent dose of $2.8 \times 10^8$ T cells/kg. No evidence of GVHD developed. In September of 1993, the patient received the same donors's PBL at an equivalent dose of $4 \times 10^7$ T cells/kg, with concomitant administration of rhIL-2 subcutaneously ($6 \times 10^6$ IU/m$^2$) for 3 consecutive days starting on the day of cell infusion. In November of 1993, the patient received ADL from the BMT donor at an equivalent dose of $1.4 \times 10^8$ T cells/kg with concomitant administration of rhIL-2 subcutaneously ($6 \times 10^6$ IU/m$^2$) for 3 consecutive days starting on the day of cell infusion. No evidence of GVHD developed. Despite the absence of GVHD, the patient showed a complete hematologic and cytogenetic response with 20 out of 20 metaphase featuring normal male karyotype with no chromosomal aberrations and normal bone marrow morphology. Unfortunately, overt relapse was noted again in January of 1994, and the patient died in February 1994 due to progressive disease.

What is claimed is:

1. A method of treating a human cancer patient having a solid tumor comprising malignant cells, said patient having undergone a cancer therapy regimen comprising allogeneic stem cell transplantation, said method comprising:

a) administering allogeneic lymphocytes to said patient; and b) monitoring said patient for levels of said malignant cells.

2. The method of claim 1, wherein said solid tumor is a breast carcinoma.

3. The method of claim 1, wherein said allogeneic lymphocytes are activated by exposure to a T-cell activator in vitro prior to administration to said patient.

4. The method of claim 3, wherein said T-cell activator comprises at least one T-cell signal transduction pathway activator.

5. The method of claim 4, wherein said T-cell activator is selected from the group consisting of IL-1, IL-2, IL-4, IL-5, IL-6, IL-7, IL-12, IL-13, IL-15, IFNα, IFNγ, TNFα, anti-CD3, anti-CD28, phytohemagglutinin, concanavalin-A and phorbol esters.

6. The method of claim 5, wherein said T-cell activator comprises IL-2.

7. The method of claim 1, wherein said allogeneic lymphocytes are administered to said patient in a series of incrementally increasing amounts, pending no or controllable graft-versus-host disease between increments.

8. The method of claim 1, wherein said allogeneic lymphocytes are HLA-compatible with said patient.

9. The method of claim 1, wherein said administration of allogeneic lymphocytes is accompanied by in vivo administration of T-cell activator.

10. The method of claim 9, wherein said in vivo administered T-cell activator is given to said patient over a time course of two to four days.

11. The method of claim 9, wherein said T-cell activator comprises at least one T-cell signal transduction pathway activator.

12. The method of claim 11, wherein said T-cell activator is selected from the group consisting of IL-1, IL-2, IL-4, IL-5, IL-6, IL-7, IL-12, IL-13, IL-15, IFNα, IFNγ, TNFα, anti-CD3, anti-CD28, phytohemagglutinin, concanavalin-A and phorbol esters.

13. The method of claim 12, wherein said T-cell activator comprises IL-2.

14. The method of claim 1, wherein said allogeneic lymphocytes are lifespan-limited.

15. The method of claim 14, wherein said allogeneic lymphocytes carry a suicide gene conferring on said lymphocytes susceptibility to killing by a chemotherapeutic agent following administration of said lymphocytes to said patient.

16. The method of claim 1, wherein said allogeneic lymphocytes are administered to said patient in the form of a peripheral blood mononuclear cell preparation.

* * * * *